United States Patent [19]
Hein et al.

[11] Patent Number: 5,499,985
[45] Date of Patent: Mar. 19, 1996

[54] DETACHABLE COUPLING SYSTEM FOR SURGICAL INSTRUMENTS

[75] Inventors: Todd J. Hein, Minneapolis; Mike K. Utley, Hopkins, both of Minn.

[73] Assignee: Orthopaedic Innovations, Inc., Minneapolis, Minn.

[21] Appl. No.: 157,480

[22] Filed: Nov. 24, 1993

[51] Int. Cl.⁶ ................................. A61B 17/56
[52] U.S. Cl. ............... 606/99; 606/86; 606/1; 24/583; 24/584
[58] Field of Search ............... 606/1, 53, 72, 606/73, 80, 81, 84, 85, 86, 87, 88, 91, 89, 92, 96, 95, 99, 100, 104; 128/722; 604/283; 24/582, 581, 583, 584, 585, 590, 597, 588, 628, 702, 663, 664, 665, 677; 30/500; 81/489; 7/167, 168; 279/19, 19.1, 76, 77, 78, 79, 80, 82

[56] References Cited

U.S. PATENT DOCUMENTS

| | | | |
|---|---|---|---|
| 3,718,340 | 2/1973 | Stewart | 606/104 X |
| 4,131,116 | 12/1978 | Hedrick . | |
| 4,212,640 | 7/1980 | Logé et al. | 433/82 |
| 4,230,327 | 10/1980 | Röhm | 279/61 |
| 4,398,322 | 8/1983 | Ewen | 24/590 X |
| 4,441,563 | 4/1984 | Walton, II | 173/163 |
| 4,585,077 | 4/1986 | Bergler | 173/48 |
| 4,676,573 | 6/1987 | Norman | 439/318 |
| 4,963,155 | 10/1990 | Lazzeri et al. | 623/23 |
| 5,057,112 | 10/1991 | Sherman et al. | 606/79 |
| 5,109,867 | 5/1992 | Twyford, Jr. | 128/772 |
| 5,122,134 | 6/1992 | Borzone et al. | 606/80 |
| 5,190,550 | 3/1993 | Miller et al. | 606/85 |
| 5,203,653 | 4/1993 | Kudla | 408/207 |

Primary Examiner—Stephen C. Pellegrino
Assistant Examiner—Guy V. Tucker
Attorney, Agent, or Firm—Jennifer K. Farrar; Janal M. Kalis

[57] ABSTRACT

A coupling system for detachably connecting a surgical tool to a driver to form a surgical instrument. The coupling system includes two members. The first member has a cylindrical body with at least one, preferably two, projection(s) or lobe(s) protruding from the body. The second member has a cylindrical recess, at least one (two if two projections are present on the opposite member) longitudinal passageway(s) adjoining the cylindrical recess, and at least one undercut recess adjoining both the cylindrical recess and the passageway. A reversible rotation blocking mechanism is also present. Preferably, an axial cannula is present in the coupling. A kit and a method of surgery are also disclosed.

5 Claims, 6 Drawing Sheets

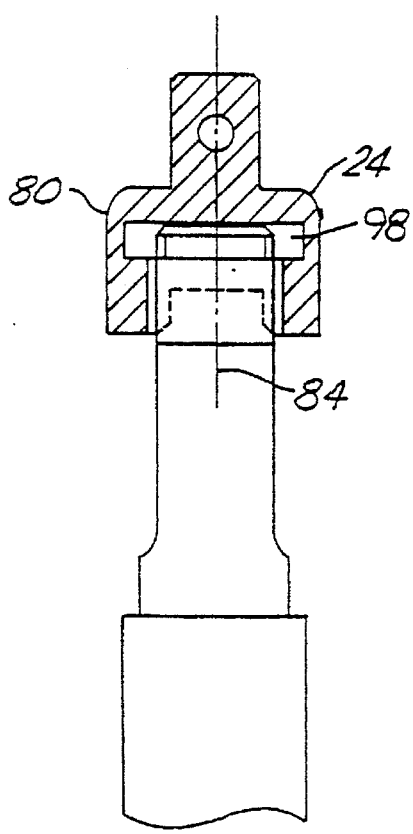
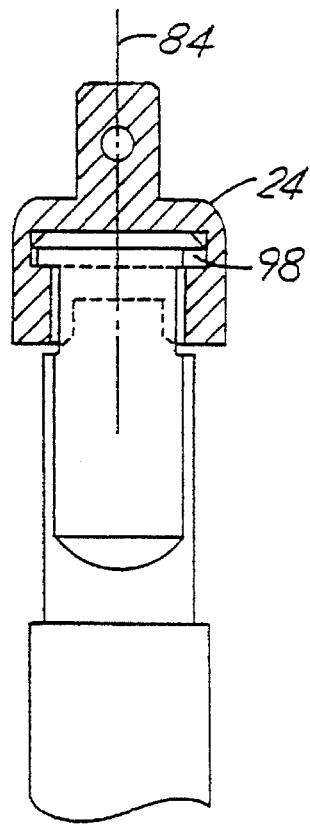
Fig. 6A
Fig. 6B
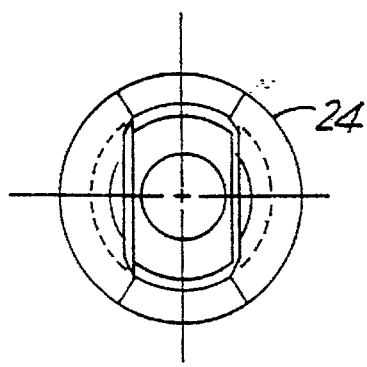
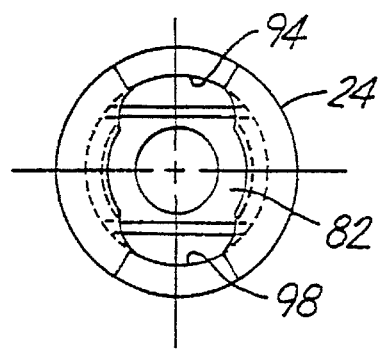
Fig. 6C
Fig. 6D

DETACHABLE COUPLING SYSTEM FOR SURGICAL INSTRUMENTS

BACKGROUND OF THE INVENTION

The present invention relates to detachable couplings for surgical instruments. More particularly, the present invention relates to detachable couplings for attaching medical tools to various drive systems including handles to form surgical instruments, such as surgical instruments for facilitating total joint arthroplasty.

By way of background, consider arthroplasty, a surgical procedure to which the present invention is particularly applicable. Total joint arthroplasty or replacement is becoming an increasingly necessary surgical procedure as the population shifts to include a greater fraction of elderly and injured populations. Such a procedure often allows a patient to function and ambulate normally. In the recent past, orthopaedic surgeons have successfully implanted cemented total joint systems into patients. Although these systems have proven generally successful over long periods, surgeons are constantly attempting to increase the success rate of total joint arthroplasty.

Total joint replacement requires an involved surgical procedure conducted by a trained surgeon. Once the tissue surrounding the wounded joint has been temporarily removed, the surgeon begins preparing the intermedullary canal of a bone for the total joint arthroplasty. In the case of hip arthroplasty, the intermedullary canal of the femur is prepared in the following manner.

The proximal end of the femoral neck is first osteotomized. A gauge or osteotomy template is placed on the femur to provide the surgeon with a reference to decide where to sever the femoral neck. Once the femoral neck is removed, the femoral canal is exposed and is ready to be prepared to accept the femoral component of a total hip prosthesis. A few instruments are used in the procedure. These include a reamer, a broach, and optionally, a box chisel. All of these instruments are commonly known in the art of orthopaedic surgery.

A reamer is first positioned into the femoral intermedullary canal. While inserting the reamer, the surgeon rotates the reamer to sever the tissue and to enlarge the intermedullary canal. When the surgeon feels that enough tissue has severed, the surgeon removes the reamer from the femoral intermedullary canal.

A box chisel is next optionally employed. The box chisel is placed in the cavity created by the reamer. The box chisel is used to prepare the femur for improved broaching and to orient the broach for proper placement and anteversion. The box chisel prepares the opening of the cavity to comply with the cross-sectional geometry of a broach which is substantially rectangular in shape. A mallet or hammer is used to chisel the bone until the box chisel reaches the appropriate depth. The box chisel is then removed.

A broaching instrument, or simply called a broach, is next inserted into the intermedullary canal to create a cavity compatible with the prosthesis geometry. The surgeon must take care to insert the length of the broach along the same axis as was formed by the reamer. The surgeon impacts the protruding surface of the broach with a mallet or slide hammer until the collar of the broach is properly seated on the severed femoral neck surface.

A provisional neck is next placed in the broach to achieve proper neck length of the prosthesis. The provisional neck is adjusted until proper reduction is achieved to allow for proper range of motion in the joint. The provisional neck is then detached and the broach is removed from the intermedullary canal.

Finally, after the preceding preparation is complete, the femur is now ready to accept the femoral stem of a hip prosthesis. The femoral stem is cemented or press-fit into place and is now ready to accept the ball portion of the joint.

In the past, surgeons have employed a flexible wire in the above-described procedure. The wire was inserted into the length of the bone before reaming. The wire served as a guide over which a flexible reamer having a longitudinal bore therein was telescopically placed. Since the wire was flexible, it did not successfully serve as a guide for intermedullary canal preparation because the guide was not stationary. Instruments placed along or over the wire were free to move within the canal as freely as if no guide wire existed. Only flexible instrumentation was used in the prior art procedures which limited the surgeon's ability to effectively prepare the bone for accepting a prosthesis. The bores in the instruments were very small in diameter since the bores only had to fit over a wire having a diameter of up to about 1 millimeter.

When preparing a bone for a prosthesis, surgeons have consistently been met with the problem of locating the central axis of a bone. Location of the central axis of the bone is critical for a successful operation. If the prosthesis is not centered, uneven weight distribution causes problems both with respect to the bone and the prosthesis. Since the entire bone is not exposed during total arthroplasty, the surgeon has only a limited view of a portion of the bone. Therefore, locating the bone's axis is exceedingly difficult. To date, orthopaedic surgeons have not had reliable methods of successfully or accurately locating a bone's central axis.

The above-described procedure is met with other difficulties. If the surgeon does not insert the broach into the same cavity that the reamer was placed, the surgeon may easily crack the patient's bone. This results in prolonged surgery and prolonged healing time. The surgeon must also take care not to create an area which is exceedingly large and therefore is not suited to receive a prosthesis.

Clearly, such a complex surgical procedure would benefit from improved instrumentation.

SUMMARY OF THE INVENTION

The present invention allows a surgeon to select and combine the various tools and handles or drive systems in a convenient yet dependable manner. The invention also promotes economic efficiency by reducing the total number of tools required to be on hand for an operation. Further, the procedure would benefit from an ability to substitute drivers for the tools easily, and even leaving the tool head in place while changing drivers. Surgeons would also be helped by a coupling which was easily changed and yet provided dependable transmission of both push/pull force and rotational forces.

The present invention, in a first embodiment, is a coupling system for detachably connecting a surgical tool head to a driver for the surgical tool head to form a surgical instrument. The coupling system includes two members. The first member has a generally cylindrical body, defining a first axis, with at least one projection, preferably two projections, protruding from the body. The second member has a body with a generally cylindrical recess, defining a second axis, at least one (two if two projections are present on the opposite member) longitudinal passageway(s) adjoining the cylindrical recess, and at least one undercut recess adjoining both the cylindrical recess and the passageway. The present invention also allows reversible blocking of rotation of the first member relative to the second member when the members are co-axially aligned and the projection is located in the undercut recess. Preferably, the means for reversibly blocking include a longitudinally movable, nonrotatable engagement means on one of the members, and a nonrotatable, acceptor means on the opposite member. By "nonrotatable" in these instances is meant that the "means" does not rotate relative to the member carrying such "means." Preferably, the longitudinally movable, nonrotatable engagement means is carried on the first member. Most preferably, the longitudinally movable, nonrotatable engagement means includes biasing means to urge the engagement means into interaction with the acceptor means to effect blocking of rotation. Preferably, the coupling system has radial symmetry, most preferably, bilateral symmetry. With such symmetry, if rotated by a drill motor, the coupling does not cause eccentric motion or wobble and does not interfere with the underlying surgical procedure. Preferably, the longitudinally movable, nonrotatable engagement means includes at least one, most preferably two lug(s). Most preferably, two bilaterally symmetrical lug receiving notches are present on the opposite member. Preferably, an axial cannula is present in the coupling.

In another embodiment, the present invention is a surgical instrument system including at least one tool head having a member of the coupling system and at least one driver for a tool head having the complementary coupling member.

In another embodiment, the present invention is a surgical instrument system kit including a plurality of drivers for a tool head, each of the tool heads having a generally cylindrical body, defining a first axis, with at least one projection radially protruding from the body and longitudinally movable, nonrotatable engagement means and a plurality of tool heads, each of the tool heads having a coupling member having a body with a generally cylindrical recess, defining a second axis, at least one longitudinal passageway adjoining the cylindrical recess, and at least one undercut recess adjoining both the cylindrical recess and the passageway, and nonrotatable, acceptor means. In this embodiment, the engagement means and acceptor means interact to reversibly block rotation of the driver relative to the tool head when the tool head and driver are co-axially aligned and the projection is located in the undercut recess. Preferably, at least one of the drivers and at least one of the tool heads include an axial cannula.

In another embodiment, the present invention is a method of surgery. The method includes the steps of: providing a tool head reversibly coupled to a first driver; providing a second driver, different from the first driver; and uncoupling the first driver from the tool and coupling the second driver to the tool. Preferably, the tool head, first and second drivers each have an axial canula. Tools which might be in the kit include a cannulated osteotomy guide, a cannulated attachment shaft, a cannulated reamer, a cannulated box chisel, and a cannulated broach. Drivers which might be in the kit include a cannulated handle, a cannulated slidehammer, and a cannulated rotary driver.

BRIEF DESCRIPTION OF THE DRAWINGS

FIG. 6A depicts the members coaxially aligned and inserted, but not rotated. FIG. 6B depicts the members coaxially aligned, inserted and rotated. FIG. 6C is an end view of FIG. 6A with some internal structure depicted in dotted lines. FIG. 6D is a sectional end view of FIG. 6B with some internal structure depicted in dotted lines.

DETAILED DESCRIPTION OF THE INVENTION

Figure 1:
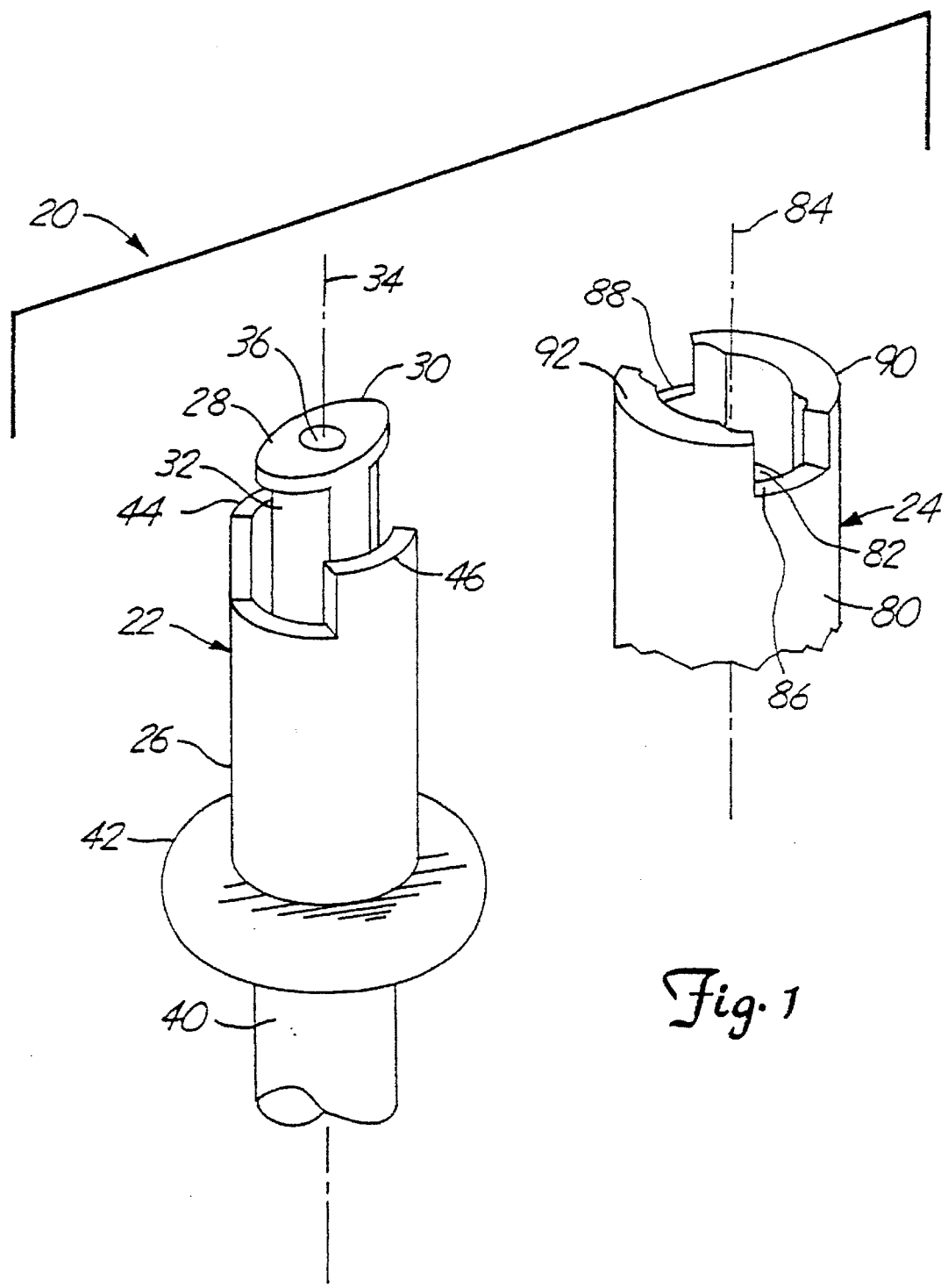
FIG. 1 is a schematic perspective view of the two members of a coupling of the present invention. Prior to attachment, one of the two members depicted in this drawing needs to be inverted and then the two members need to be coaxially aligned.

In a preferred embodiment, the present invention, as schematically depicted in FIG. 1, includes a coupling 20. The coupling 20 has two primary members 22 and 24, which are preferably at ends of a surgical tool and a driver, such as for example a handle or slide hammer. Preferably, though not always necessarily, the driver carries member 22, which includes a sleeve 26, and the tool carries member 24. For ease of explanation hereafter these members may be termed tool member 24 and driver member 22.

The members 22 and 24 of the coupling 20 serve to provide a strong, yet easily detachable, mechanical connection between a surgical tool and a driver for the surgical tool, thereby forming a surgical instrument. Preferably, the surgical instrument, is formed from a kit with an array of different tools, each of the tools having a tool member 24 and an array of different drivers each having driver member 22. The kit provides economy and additionally the ability to change drivers on a tool which is in use. For example, in the surgical procedure of total joint replacement or arthroplasty, it may sometimes be advantageous to a surgeon preparing an intermedullary canal of the femur associated with a hip to be replaced to change from a handle for pushing and tapping with a mallet to a slide hammer when driving a box chisel. Tools which advantageously are present in a kit for arthroplasty are reamers, box chisels, and broaches, optionally each having an axial cannula adapted to telescopically advance or retract over a guide wire or guide rod. Drivers which advantageously are present in a kit for arthroplasty are handles, slide hammers, and rotary drivers (similar to drill motors) or extensions for rotary drivers which adapt from a Jacobs jaw chuck to the coupling 20. Preferably, most of the drivers are cannulated. The coupling 20 is fully consistent with cannulation communication between the driver and the tool.

To join a tool to a driver with this coupling system 20, one merely retracts the sleeve 26, inserts the driver member 22 into the tool member 24 while coaxially aligned, rotates the tool member 22 about 90° (note FIGS. 6A and 6B, 6C and 6D) and releases the sleeve 26 to lock the coupling 20. If the tool is engaged, this is a one-handed step for the surgeon.

The driver member 22 has a first lobe 28 and an opposed second lobe 30 each projecting from a generally cylindrical body 32. Optionally, but preferably, the body is cannulated along its axis 34, thereby providing an internal channel or cannula 36. The body also has longitudinally extending flats 38 on opposing sides, offset from the lobes 28 and 30 by about 90°.

Figure 4A:
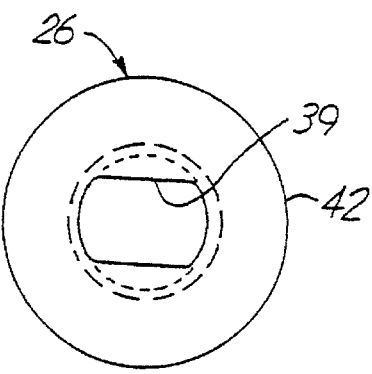
FIG. 4A is a top plan view of an end of the sleeve of FIG. 2A with some internal structure shown in dotted lines.

The driver member 22 also has sleeve 26 which is longitudinally movable along body 32 and shaft 40 which continues to the main driver (not shown in FIG. 1). The sleeve 26 includes a shoulder 42, preferably at or near the proximal end of the sleeve 26, such as is shown in FIG. 4A. The shoulder 42 aids the surgeon in retracting the sleeve 26 against an internal biasing system which urges the sleeve distally toward the lobes 28 and 30. The sleeve 26 also has distally located lugs 44 and 46, which are offset from the lobes 28 and 30 by 90° of rotation about the axis 34.

The tool member 24 also has a body 80 with an axial cylindrical recess or bore 82 along axis 84. The body 80 has two lug acceptors or notches 86 and 88 between two lugs 90 and 92. The bore 82 has two opposed passageways 94 (and 96, not visible in FIG. 1) interposed between the lugs 90 and 92 and aligned with the notches 86 and 84. The passageways 94 and 96 enable insertion or passage of the lobes 28 and 30 into the tool member 24. Adjoining the passageways 94 and 96 is an axially centered undercut recess 98 which is of larger diameter than the axial bore 82 and accommodates the diameter or expanse between the extreme projection of lobe 28 and lobe 30. The undercut recess 98 allows the lobes to rotate about 90° when inserted into the tool member to the depth of the undercut recess 98. Due to an interference fit between the two members, rotation is optionally allowed in only a single direction and rotation past 90° is inhibited.

Figure 2A:
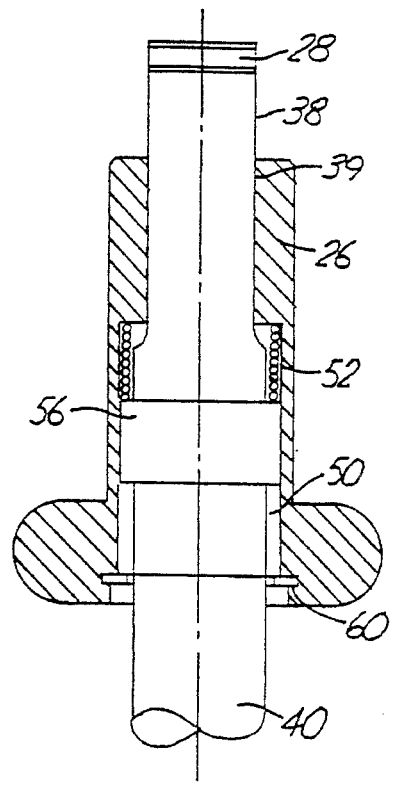
FIG. 2A depicts the sleeve in the rotation blocking position.
Figure 2B:
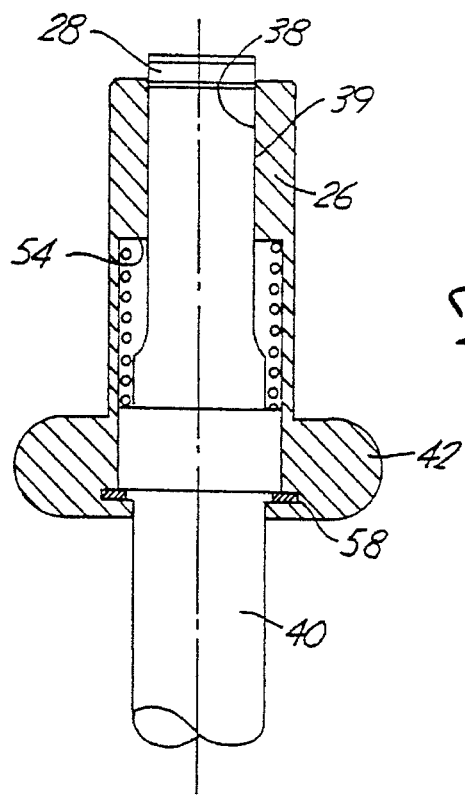
FIG. 2B depicts the sleeve in a retracted position on a portion of shaft. This retracted position allows rotation between the members.
Figure 4B:
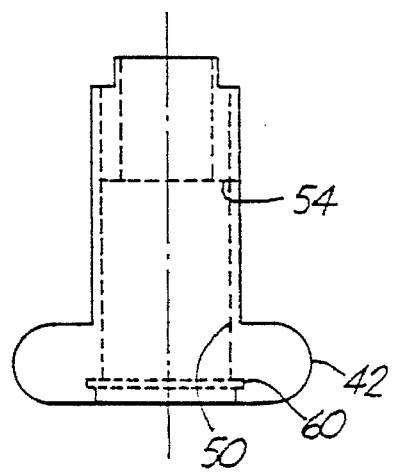
FIG. 4B is a front view of the sleeve of FIG. 2A.
Figure 4C:
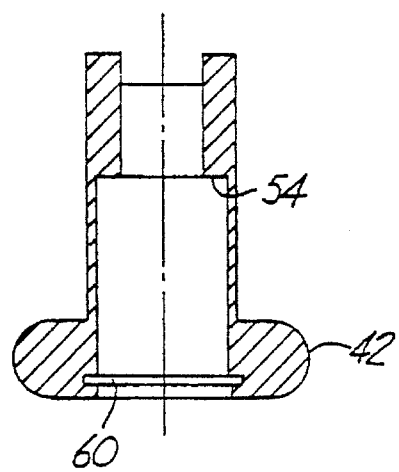
FIG. 4C is a sectional view at A—A of FIG. 4A.

When connected in the above described manner, the two members 22 and 24 can transmit force from the driver to the tool in many directions. Longitudinal, (i.e. push or pull force) is particularly well transmitted. However, a twisting force which might turn the lobes 28 and 30 out of the undercut recess 98 is not possible absent a mechanism to prevent uncoupling. That rotation is blocked, however, by allowing the sleeve 26 to advance distally to insert the lugs 44 and 46 in notches 86 and 88. As shown in FIGS. 2A and 2B, sleeve 26 includes an internal recess 50 which includes a spring 52. Spring 52 is captured between the distal terminus 54 of internal recess 50 and a ring 56 on shaft 40. Ring 56 is, in turn, captured by a lock ring 58 and groove 60 also shown in FIGS. 4B and 4C at the proximal end of internal recess 50. The spring 52 urges the sleeve 26 distally on shaft 40 until it is stopped by ring 56 contacting lock ring 58 or when the coupling is in use by the lugs 44 and 46 filling notches 86 and 88. Rotation of the sleeve 26 is prevented by flats 38 and complementary structure 39 in the sleeve 26.

Figure 3:
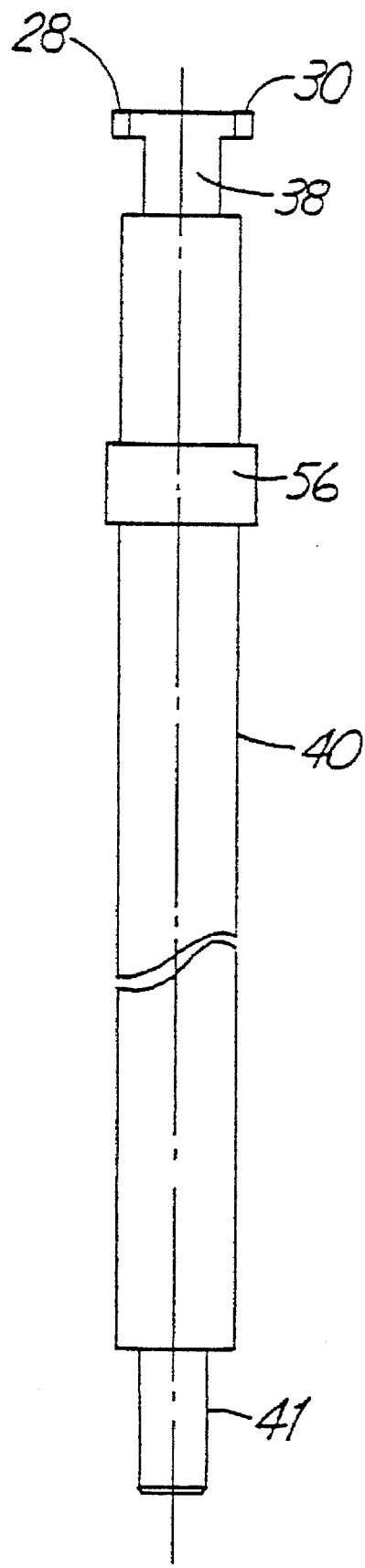
FIG. 3 is a front view of the shaft portion of the member depicted in FIG. 2.

A representative driver, specifically suitable as a handle blank, is shown in FIG. 3. A disk handle (not shown) may be mounted at proximal end 41, opposite from the coupling member 22 on the distal end of shaft 40. Alternatively, proximal end 41 may be placed in a Jacobs chuck and driven by a drill-like appliance. Alternatively, a slide hammer may be fitted over the shaft 40.

Figure 5A:
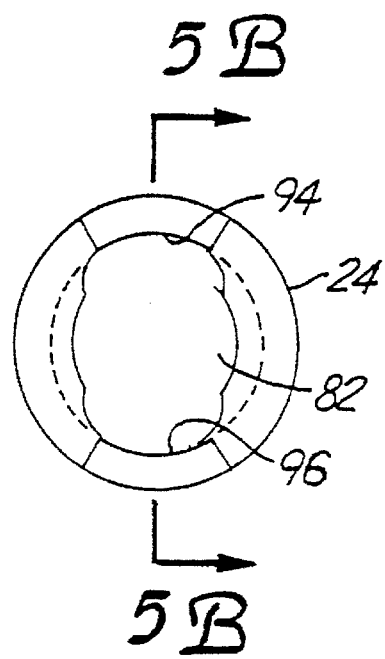
FIG. 5A is a bottom plan view of an end of the second member.
Figure 5B:
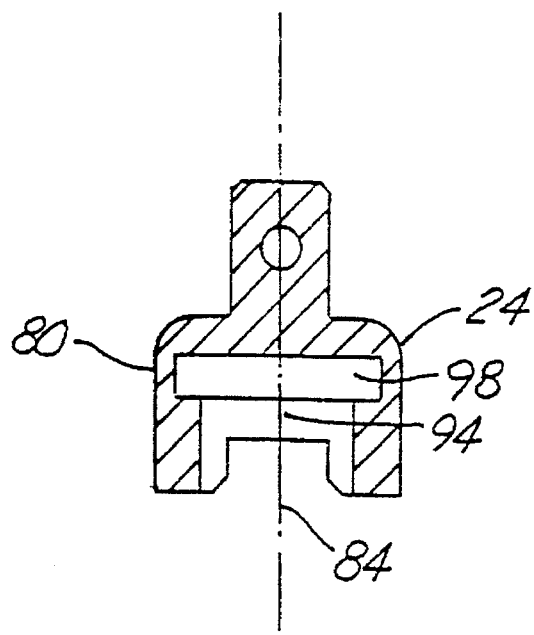
FIG. 5B is a sectional view at B—B of FIG. 5A.

A representative tool member 24 is shown in FIGS. 5A and 5B. The member's body 80 need not be cylindrical as shown and certain arthroplasty tools lack a cylindrical body such as certain reamers. The particular member depicted is for connection to a reamer through a square drive which may be pinned or have a spring loaded projection to retain its connection. Other optional tools preferably have the tool member 24 integral with tool and preferably include an axial cannula.

Preferably surgical grade stainless steel is the material of choice for fabrication of surgical instruments employing the coupling system of this invention.

One skilled in the art will recognize that the details of the previous embodiment may be varied without departing from the spirit and scope of the invention.

We claim:

1. A coupling system for detachably connecting a surgical tool head to a driver for the surgical tool head to form a surgical instrument, the coupling system comprising:

a first member having a generally cylindrical body, defining a first axis, with at least one projection protruding from the body;

a second member having a body defining a cylindrical recess, with a second axis, the body enclosing at least one passageway adjacent to the cylindrical recess, and defining at least one undercut recess adjacent to both the cylindrical recess and the passageway; and means for reversibly blocking rotation of the first member relative to the second member when the members are coaxially aligned and the projection is located in the undercut recess comprising longitudinally movable, non-rotatable engagement means comprising at least one lug that is one of two bilaterally symmetrical lugs, on one of the members, and non-rotatable, acceptor means on the opposite member wherein the acceptor means has two bilaterally symmetrical lug receiving notches.

2. The coupling system of claim 1 and wherein the longitudinally movable, nonrotatable engagement means is carried on the first member.

3. The coupling system of claim 1 and wherein the longitudinally movable, nonrotatable engagement means includes biasing means to urge the engagement means into interaction with the acceptor means to effect blocking of rotation.

4. A surgical coupling system comprising:

a tool head;

a first coupling member having a generally cylindrical body, defining a first axis, with at least one projection protruding from the body, the first coupling member receiving the tool head;

a driver for the tool head; and a second member having a body defining a cylindrical recess, with a second axis, the body enclosing at least one passageway adjacent to the cylindrical recess, and defining at least one undercut recess adjacent to the cylindrical recess in the passageway, the second member receiving the driver; and means for reversibly blocking rotation of the first member relative to the second member when the members are coaxially aligned and the projection is located in the undercut recess comprising longitudinally movable, nonrotatable engagement means comprising at least one lug that is one of two bilaterally symmetrical lugs, on one of the members, and nonrotatable acceptor means on the opposite member wherein the acceptor means has two bilaterally symmetrical lug receiving notches.

5. A surgical instrument system kit comprising:

a plurality of drivers for a tool head, each of the tool drivers having a generally cylindrical body, defining a first axis, with at least one projection radially protruding from the body and longitudinally movable, nonrotatable engagement means comprising at least one lug that is one of two bilaterally symmetrical lugs, on one of the members and non-rotatable, acceptor means on the opposite member wherein the acceptor means has two bilaterally symmetrical lug receiving notches;

a plurality of tool heads, each of the tool heads having a coupling member having a body defining a generally cylindrical recess, with a second axis, at least one passageway adjacent to the cylindrical recess, and at least one undercut recess adjacent to both the cylindrical recess and the passageway, and non-rotatable, acceptor means; and wherein the engagement means and acceptor means reversibly block rotation of the driver relative to the tool head when the tool head and driver are co-axially aligned and the projection is located in the undercut recess.

* * * * *